United States Patent [19]

Lane et al.

[11] Patent Number: 4,656,031
[45] Date of Patent: Apr. 7, 1987

[54] DENTIFRICE COMPOSITIONS

[75] Inventors: Roger M. Lane, Merseyside; Derek M. C. Hull, Cheshire; Charles A. Saxton, Merseyside; Franciscus J. G. van der Ouderaa, Cheshire, all of England

[73] Assignee: Lever Brothers Company, New York, N.Y.

[21] Appl. No.: 731,224

[22] Filed: May 7, 1985

[30] Foreign Application Priority Data

May 9, 1984 [GB] United Kingdom ............... 8411731

[51] Int. Cl.$^4$ ............................................. A61K 9/16
[52] U.S. Cl. ................................................... 424/49
[58] Field of Search ................................. 424/49–58

[56] References Cited

U.S. PATENT DOCUMENTS

| | | | |
|---|---|---|---|
| 2,588,324 | 3/1952 | Lewis et al. | 167/93 |
| 3,784,698 | 1/1974 | Model et al. | 424/311 |
| 3,897,548 | 7/1975 | Katz | 424/54 |
| 4,022,880 | 5/1977 | Vinson et al. | 424/49 |
| 4,082,841 | 4/1978 | Pader | 424/50 |
| 4,100,269 | 7/1978 | Pader | 424/49 |
| 4,111,844 | 9/1978 | Polony et al. | 252/106 |
| 4,144,323 | 3/1979 | Lamberti | 424/54 |
| 4,152,418 | 5/1979 | Pader | 424/50 |
| 4,154,815 | 5/1979 | Pader | 424/50 |
| 4,294,894 | 10/1981 | Vellucci | 424/49 |
| 4,425,325 | 10/1984 | Ritchey | 424/54 |
| 4,515,704 | 5/1985 | Akred et al. | 252/DIG. 14 |
| 4,522,806 | 6/1985 | Muhlemann | 424/52 |

FOREIGN PATENT DOCUMENTS

| | | |
|---|---|---|
| 1302019 | 1/1973 | United Kingdom . |
| 1305353 | 1/1973 | United Kingdom . |
| 1373001 | 11/1974 | United Kingdom . |
| 1373003 | 11/1974 | United Kingdom . |
| 1459026 | 12/1976 | United Kingdom . |

OTHER PUBLICATIONS

Journal of Clinical Periodontology 1980: 7, 432–442.
British Dental Journal, Mar. 1984, 175–178.
Cosmetics Science & Technology, vol. 1, 1972, p. 504.

*Primary Examiner*—Shep K. Rose
*Attorney, Agent, or Firm*—Matthew J. McDonald; James J. Farrell

[57] ABSTRACT

It is disclosed that a dentifrice which includes a surfactant and an anti-plaque agent comprising a substantially water-insoluble non-cationic antimicrobial agent or a zinc salt or a mixture thereof has enhanced activity when the dentifrice comprises at least 0.2% by weight of a lamellar liquid crystal surfactant phase having a lamellar spacing of less than 6.0 nm.

22 Claims, No Drawings

DENTIFRICE COMPOSITIONS

This invention relates to dentifrice compositions, more particularly to dental creams or gels, for inhibiting the formation of dental plaque.

It is now established that there is a relationship between dental plaque and gingival inflammation. At present, mechanical cleaning by toothbrushing is the most widely used method of removing plaque. However, the relatively short period of brushing commonly practised is insufficient to achieve adequate removal of plaque especially from areas least accessible to brushing.

The dental literature over the last 25 years is replete with publications concerned with the use of organic antimicrobial agents to combat dental plaque. Most work has concentrated on the use of cationic agents because these are substantive to oral tissues and are therefore retained in the mouth. It is believed that their activity is due to their being adsorbed onto oral surfaces and gradually released over a period of time (Journal of Clinical Periodontology 1980: 7 431–442). Unless an active antimicrobial agent is adsorbed onto oral surfaces the oral bacteria in the mouth rapidly recover and no significant reduction in plaque growth would be expected (British Dental Journal March 1984, 175–178). However, the successful formulation of a cationic antimicrobial agent into a commercially acceptable toothpaste has not yet been achieved and this is at least in part due to the incompatibility of cationic antimicrobial agents with common toothpaste ingredients. In addition, cationics, especially chlorhexidine which has been extensively investigated, have the further disadvantage of causing tooth staining as well as having a long-lasting bitter taste. Many cationics also cause irritation of the oral tissues. Attempts to overcome the tooth staining problem are the subject of many patents. We believe that there is to date no commercial toothpaste containing an organic cationic antimicrobial agent which is recognised as having a significant anti-plaque benefit.

Although there are references in the literature to attempts to use antimicrobial agents other than cationic compounds for providing an improvement in oral health it is generally considered that the oral substantivity of these agents is not sufficient to provide a significant antiplaque benefit and they are in any case considered unattractive because of their generally poor water-solubility. Hitherto it has been the general belief that it is necessary for the active agent of a dentifrice to be in solution in the aqueous phase of the toothpaste.

We have now discovered that it is possible to obtain substantial reductions in plaque growth by means of a substantially water-insoluble non-cationic antimicrobial agent, or mixture of antimicrobial agents, provided the dentifrice composition containing it has certain characteristics of which details are given below. Such unexpected anti-plaque activity we believe is due to the fact that the special dentifrice composition of the invention is able to deliver the antimicrobial agent to tooth surface where it is retained for a time sufficient to materially affect the rate of plaque regrowth, rate of plaque metabolism and equilibrium plaque level.

Our research has also shown that our special dentifrice composition is also able to lead to an enhanced retention in the mouth of zinc salts, generally known to have an anti-plaque effect, resulting in an improvement in effectiveness in inhibiting plaque growth. Various zinc salts, for example zinc citrate, are referred to in U.S. Pat. No. 4,022,880. The use of zinc carboxymethyloxysuccinate is referred to in U.S. Pat. No. 4,144,323.

According to the present invention there is provided a dentifrice composition effective to inhibit the growth of dental plaque comprising a surfactant and an antiplaque agent consisting of a substantially water-insoluble non-cationic antimicrobial agent or a zinc salt having a water solubility greater than $2 \times 10^{-4}$ g, preferably greater than $1 \times 10^{-2}$ g, per 100g of water at 25° C. and at pH7, or a mixture thereof, characterised in that there is present in the dentifrice composition a lyotropic lamellar liquid crystal phase comprising alternate layers of surfactant molecules and water molecules (and hereinafter referred to as a lamellar liquid crystal surfactant phase) having a lamellar spacing of less than 6.0 nm, the lamellar liquid crystal surfactant phase being present in an amount of at least 0.2%, preferably at least 0.3%, and more preferably at least 0.5%, by weight of the dentifrice composition.

The determination of whether a dentifrice composition comprises a lamellar liquid crystal surfactant phase can be determined by examination of the product obtained by subjecting the dentifrice to a centrifuge separation procedure, which will now be described.

The dentifrice is centrifuged with sufficient centrifugal force to separate the main phases present which usually are abrasive, aqueous, detergent and flavour phases. A preliminary centrifugation is convenient to separate the majority of the abrasive, followed by an ultracentrifugation to separate the phases of the liquid portion. The speed and duration of the centrifugation required is dependent upon the resistance of the formulation towards separation. The separation of a dentifrice containing sodium carboxymethylcellulose as binder is facilitated by degrading the binder enzymatically prior to centrifugation. The dentifrice is incubated with cellulase-containing powder (0.1% w/w, prepared from Aspergillus niger, activity 1.3 units/mg) for 18 hours at room temperature to degrade the sodium carboxymethylcellulose binder.

The resultant slurry or the dentifrice itself, if no preliminary degradation of the binder is carried out, is centrifuged at 10,000 xg for 1 hour and the sedimented abrasive removed. The liquid portion is then ultracentrifuged at 200,000xg for 2 hours or until there is no substantial change in the volumes of the separated layers. These conditions of centrifugation have generally been found to be satisfactory for separating the phases of a dentifrice although longer periods of centrifugation and ultracentrifugation may sometimes be necessary.

The product obtained by this centrifuge procedure is referred to herein as the centrifuge separation product. The centrifuge separation product will consist of a number of layers. The lower layer of solids and the humectant-containing layer above it will together constitute the major part of the centrifuge separation product. The remainder of the centrifuge separation product may include a layer consisting predominantly of surfactant in the form of liquid crystals. If present, this layer will generally constitute the upper layer or one of the upper layers. Its actual position will depend on the relative densities of the layers. This layer constituting the liquid crystal surfactant phase of the dentifrice can be removed from the centrifuge separation product and its weight as a percentage of the dentifrice determined. The lamellar liquid crystal surfactant phase is basically made up of layers of surfactant molecules separated by water layers but may comprise other components depending upon the overall composition of the dentifrice. The distribution of such other components between the surfactant and water layers will depend upon their respective aqueous solubilities and hydrophobicities.

Liquid crystals are well known and a recent book describing them is entitled "Aggregation Processes in Solution" edited by E Wyn-Jones and J Gormally published by Elsevier Scientific Publishing Company, Amsterdam-Oxford-New York 1983, and particular reference is made to Chapter 7 entitled "Lyotropic Liquid Crystals".

If the centrifuge separation product comprises a lamellar liquid crystal surfactant phase then the layer spacing can be determined by an X-ray scattering technique.

The layer spacing, $d_o$, is defined as the distance between repeat units in the cross-section of a layered liquid crystal structure, i.e., the combined thickness of the detergent sheet and of the water layer sandwiched between the detergent sheets. It can be measured by Small Angle X-ray Scattering (SAXS), a technique used to determine long periodicities in the range 1 nm–1,000 nm in crystalline or liquid crystal materials. The 'Kratky' SAXS camera used in such work produces, through a sophisticated collimation system, a fine beam of X-rays (Cu, $K_\alpha$ radiation) which impinge on the sample contained in a 1 mm glass capillary or sandwiched between 6μ thick Mylar film.

The scattered radiation is detected by a proportional counter which determines the variation in scattered intensity with respect to angle. The angle corresponding to the peak maximum is measured from the chart recorder trace and the corresponding 'd-spacing' is calculated from Bragg's equation $$2d \sin \theta = n \lambda$$

with n=1, λ=0.1542 nm for Cu $K_\alpha$ radiation.

Applications of this technique for the measurement of the lamellar spacing of lamellar liquid crystal phases are described in Journal of Colloid and Interface Science, Vol. 41, No. 1, April 1974, pages 59 to 64 and Vol. 86, No. 2, April 1982, pages 501 to 514.

The lamellar spacing of the liquid crystal surfactant phase of a dentifrice according to the present invention is preferably less than 5.0 nm, more preferably less than 4.4 nm.

Dentifrices usually comprise an anionic surfactant and most commonly used is sodium lauryl sulphate derived from coconut fatty acids comprising mainly sodium dodecyl sulphate, although pure sodium dodecyl sulphate can be used. Sodium dodecylbenzene sulphonate is another known dentifrice surfactant although it is not usually employed as the sole surfactant of a dentifrice. It may be used in combination with sodium lauryl sulphate. Suitable combinations of sodium lauryl sulphate and sodium dodecyl benzene sulphonate are in the proportions 4:1 to 1:4 by weight. The use of a combination of these surfactants in a dentifrice comprising a zinc-containing anti-plaque agent is described in GB-A No. 1 373 003. Sodium lauroyl sarcosinate is another well-known dentifrice surfactant that may also be employed in dentifrices of this invention.

The surfactant in a dentifrice can be present in three main forms, as a solution, a liquid crystal phase or crystalline solid. The form or forms in which the surfactant is present depends particularly on the other ingredients of the dentifrice. Thus in the presence of glycerol, which is very commonly used as the sole or major humectant liquid, the surfactant will generally be present as a solution since glycerol is a solvent for common dentifrice surfactants. The same applies to propylene glycol, also a well-known dentifrice humectant. We have also found that when sorbitol is employed as the humectant then in the absence of a flavour oil the surfactant is present as a solid crystalline phase due to its poor solubility in sorbitol solution. However, in the presence of flavour oil the solid crystalline surfactant phase is converted into a lamellar liquid crystal phase. Thus dentifrice formulations that promote the formation of a liquid crystal surfactant phase are those based on the use of sorbitol as the humectant and which also contain a flavour oil. However, the use in combination with sorbitol of such amounts of glycerol that do not prevent the formation of a liquid crystal surfactant phase is permissible. Other ways of producing a lamellar liquid crystal surfactant phase are, of course, within the scope of the present invention.

The layer spacing of a liquid crystal surfactant phase in a dentifrice is influenced by the electrolyte concentration of the aqueous phase. Thus the obtaining of a layer spacing of less than 6.0 nm in accordance with this invention can be effected by control of the electrolyte concentration of the aqueous phase. In order to achieve such a low lamellar spacing the electrolyte concentration needs to be relatively high. However, means other than control of electrolyte concentration may be employed to control lamellar spacing.

An appropriate concentration of the electrolyte can be produced by the addition of a suitable water-soluble electrolyte. Only simple experimentation is required to determine the amount of electrolyte required to give a low $d_o$ value. In general, any non-toxic salt or mixture of salts that is compatible with the therapeutic ingredient or ingredients, as well as with the other dentifrice components, and is organoleptically acceptable can be used. The salt that is referred to here is in addition to any fluorine-containing salt which may be included to give an anti-caries benefit. Such salt is of course, in addition to the surfactant (which is also an electrolyte) and any zinc salt which may also be present. The additional salt is also to be distinguished from a binder or thickener for the aqueous humectant liquid phase, said binder or thickener being a commonly employed dentifrice ingredient and which may be constituted by a salt, e.g., sodium carboxymethylcellulose. The surfactant, binder and fluorine-containing salts when employed at conventional levels do not produce, even in combination, a sufficient concentration of electrolyte to reduce the layer spacing of a surfactant liquid crystal phase to below 6.0 nm.

The cation of the added salt is preferably sodium, potassium, aluminium, magnesium or zinc. Suitable anions are acetate, chloride, citrate, gluconate, lactate, sulphate, phosphate, tartrate, glyconate and ascorbate. Some salts are more effective than others in reducing the $d_o$ value at the same molar cation addition. Preferred salts are those of sodium and aluminium.

We have found that the amount of sodium chloride added is suitably in the range from about 0.1 to about 3%, preferably about 0.1 to about 1%, by weight of the dentifrice composition. Other salts may be added in such amounts that the total cation molar concentration corresponds to those for sodium chloride previously given.

It is not advisable to include any more salt than is necessary to produce the desired low lamellar spacing. Excessive amounts may not only impair the organoleptic qualities of the dentifrice but in fact will result in the destruction of the liquid crystal phase. We have found that a liquid crystal surfactant phase may be destroyed on the addition of 5% sodium chloride. Consequently, it is recommended that the amount of any added electrolyte should not exceed the cation molar equivalent of about 3% by weight of the dentifrice of sodium chloride. In practice, an optimum reduction in layer spacing can be achieved at levels of addition of sodium chloride substantially less than 3% by weight.

A zinc salt, if present, will contribute to the total electrolyte concentration of the aqueous phase.

A part of the electrolyte present in the aqueous phase may be composed of ions originating from a solid abrasive agent, for example aluminium ions from an alumina abrasive, and the proportion of such ions in the aqueous phase can be dependent upon the type of mixer employed, more especially upon the energy employed in mixing the solid components during the manufacture of the dentifrice.

The dentifrices of this invention generally have a weight of liquid crystal surfactant phase of at least 1% and they typically have a content thereof of from 1.5 to 12% by weight.

The antiplaque agent of the dentifrice of the invention is a substantially water-insoluble non-cationic antimicrobial agent or a zinc salt as defined above or a mixture thereof. By a substantially water-insoluble antimicrobial agent is meant herein one having a solubility in water at 25° C. of less than 1%, preferably less than 0.5% and more preferably less than 0.1%, save that if the antimicrobial agent contains ionisable groups the solubility is determined at a pH at which such groups are not ionised. The antimicrobial agents employed in dentifrice compositions of this invention can be regarded as essentially non-ionic in character. However, many suitable antimicrobial compounds contain one or more phenolic hydroxy groups which may be ionisable at certain pHs and therefore it is considered more exact to describe the general class of antimicrobial agents useful in the dentifrice composition of this invention as being non-cationic in nature.

Examples of classes of non-cationic antimicrobial agents which may be employed in the dentifrice composition of the invention are the phenolic and bisphenolic compounds, halogenated diphenyl ethers, benzoate esters and carbanilides.

Illustrative of the phenolic antimicrobial compounds, which include the halogenated salicylanilides, are
2-phenylphenol
4-chlorophenol
4-chloro-2-methylphenol
4-chloro-3-methylphenol
4-chloro-3,5-dimethylphenol
2,4-dichloro-3,5-dimethylphenol
3,4,5,6-tetrabromo-2-methylphenol
5-methyl-2-pentylphenol
4-isopropyl-3-methylphenol
5-chloro-2-hydroxydiphenylmethane
4',5-dibromosalicylanilide
3,4',5-trichlorosalicylanilide
3,4',5-tribromosalicylanilide
2,3,3',5-tetrachlorosalicylanilide
3,3',4,5'-tetrachlorosalicylanilide
3,5-dibromo-3'-trifluoromethylsalicylanilide
5-n-octanoyl-3'-trifluoromethylsalicylanilide Among the bisphenolic compounds may be mentioned
2,2'-methylenebis(3,4,6-trichlorophenol)
2,2'-methylenebis(4-chlorophenol)
2,2'-methylenebis(4-chloro-6-bromophenol)
bis(2-hydroxy-3,5-dichlorophenyl) sulphide
bis(2-hydroxy-5-chlorophenyl) sulphide.

These antibacterial agents may be employed in the form of their zinc derivatives many of which are disclosed in U.S. Pat. No. 4,022,880.

Exemplifying the class of the halogenated hydroxydiphenyl ethers are the compounds 2',4,4'-trichloro-2-hydroxy-diphenyl ether and 2,2'-dihydroxy-5,5'-dibromo-diphenyl ether.

Another well-known class of non-cationic antimicrobial agents are the esters of p-hydroxybenzoic acid, especially the methyl, ethyl, propyl, isopropyl, butyl, isobutyl, hexyl, heptyl and benzyl esters.

Halogenated carbanilides can also be used, which class is typified by
3,4,4'-trichlorocarbanilide
3-trifluoromethyl-4,4'-dichlorocarbanilide
3,3',4-trichlorocarbanilide Other known substantially water-insoluble non-cationic antimicrobial agents can also be used, for example 2,4-dichlorobenzyl alcohol, 3,4-dichlorobenzyl alcohol and 3-(4-chlorophenoxy)-propan-1,2-diol.

The preferred antimicrobial agents are halogenated bisphenolic compounds, and the halogenated hydroxydiphenyl ethers. Especially preferred are 2',4,4'-trichloro-2-hydroxy-diphenyl ether (hereafter referred to as Triclosan) and 2,2'-methylene bis(4-chloro-6-bromophenol).

The above-mentioned antimicrobial agents which are suitable for use in dentifrices are not antibiotics. Antibiotics are not generally used so as to avoid the risk of resistant strains of bacteria developing.

The antimicrobial agent will usually be used in an amount of 0.01 to 5%, preferably 0.05 to 1% by weight of the dentifrice. A mixture of antimicrobial agents may of course be used.

The anti-plaque agent of the dentifrice composition of the invention alternatively may be a zinc salt having a water solubility greater than $2 \times 10^{-4}$ g, preferably greater than $1 \times 10^{-2}$ g, per 100 g of water at 25° C. and at pH7. Many suitable zinc salts are described in U.S. Pat. No. 4,022,880. Preferred zinc salts are those of mono-, di- and tricarboxylic acids, alpha-hydroxy carboxylic acids and amino acids Examples of preferred salts are zinc citrate, zinc tartrate, zinc malate, zinc lactate, zinc glycinate, zinc glycolate, zinc succinate, zinc carboxymethyloxysuccinate, zinc gluconate, zinc salicylate, zinc histamine and zinc histidine. Ammonium and alkali metal zinc citrates as described in U.S. Pat. No. 4,325,939 may also be used. More than one zinc salt can be of course be employed.

The zinc salt, or mixture of zinc salts, is desirably used in an amount such as to provide in the dentifrice from about 0.05 to about 1.5% by weight of zinc.

The preferred zinc salt is zinc citrate. This is readily available as the trihydrate. This is preferably incorporated in an amount of about 0.2 to about 5% by weight, and for best organoleptic acceptability most preferably 0.2 to 2% by weight.

Best results are obtained by using an antimicrobial agent in combination with a zinc salt, such as zinc citrate. Most preferred antiplaque systems are based on the combination of Triclosan and zinc citrate and the combination of 2,2'-methylenebis(4-chloro-6-bromophenol) and zinc citrate. Combinations of an antimicrobial agent and zinc citrate give the best degree of plaque growth inhibition, the most preferred combination being that of Triclosan and zinc citrate. With the latter combination a plaque inhibition approaching that obtainable with chlorhexidine has been obtained without the severe drawbacks associated with the use of that cationic material.

A particularly preferred dentifrice composition according to the invention comprises 0.05 to 0.3% Triclosan, 0.3% to 1.5% zinc citrate, 0.2 to 1% sodium chloride and 1 to 3% sodium lauryl sulphate.

The dentifrice composition of the invention preferably also comprises a particulate abrasive agent compatible with the active ingredients of the toothpaste. Especially preferred are hydrated alumina and silica abrasives, both of which are widely employed in commercial products. The particle size of the abrasive agent will usually be in the range 2 to 20 microns as is customary. Suitable grades of alpha-alumina trihydrate are sold under the name BACO by BA Chemicals of Great Britain and under the name MARTINAL by Martinswerke GmbH of Germany. Preferred silica abrasives are the well-known silica xerogels, for example GASIL 200 (sold by Crosfield Chemicals, Great Britain) and SYLOID 63 (sold by Grace Corporation USA), and precipitated silicas, for example ZEO 49 (sold by the Huber Corporation USA). The amount of abrasive agent employed will usually be between 5 and 60% by weight of the dentifrice composition.

Suitable binders or thickeners for use in dentifrice compositions are known to those skilled in the art. Commonly used are sodium carboxymethylcellulose and xanthan gum. For flavouring dentifrices peppermint and spearmint oils are commonly used, although a wide variety of other oils also find application. Flavour oils are usually present in an amount of from 0.1 to 5% by weight. Apart from the above generally standard ingredients, a number of optional ingredients may also be included, especially fluoride, such as sodium monofluorophosphate or sodium fluoride, opacifying agent, e.g. titanium dioxide, preservative, sweetening agent and a pH-adjusting agent.

The water content of the dentifrices in accordance with this invention will generally be between about 25 and 60% by weight of the dentifrice excluding insoluble solids.

The dentifrices of the invention can be made by conventional methods. Since the obtaining of a low $d_o$ spacing of a liquid crystal surfactant phase is controlled by the concentration of the electrolyte in the aqueous phase of the final toothpaste composition, water loss during manufacture affects the electrolyte concentration. It is therefore desirable to avoid the use or production of excessive temperatures during manufacture and preferably the temperature of processing is within the range 15° to 35° C., more preferably 22° to 32° C.

The present invention in one aspect relates to a process for making a dentifrice composition which includes added sodium chloride or other water-soluble salt, which process comprises mixing the water-soluble salt with the other ingredients so as to result in an aqueous phase having an electrolyte concentration sufficient to result in the formation of a liquid crystal surfactant phase having a lamellar spacing of less than 6.0 nm, the dentifrice ingredients preferably being mixed at a temperature within the range 15° to 35° C., more preferably 22° to 32° C.

The following Examples illustrate the invention. Percentages are by weight.

EXAMPLE 1

A number of toothpastes were made from the following ingredients.

| Ingredient | % |
| --- | --- |
| Alumina trihydrate | 50.000 |
| Sorbitol syrup (70% solution) | 27.000 |
| Sodium lauryl sulphate | 1.875 |
| Sodium dodecylbenzenesulphonate | 0.625 |
| Sodium carboxymethylcellulose | 0.800 |
| Zinc citrate trihydrate | 1.000 |
| Triclosan | 0.500 |
| Sodium monofluorophosphate | 0.850 |
| Flavour oil | 1.200 |
| Sodium saccharinate | 0.180 |
| Formalin BP | 0.040 |
| Water | to 100.000 |

The toothpastes were made using a variety of toothpaste mixers some mixers having a greater energy of mixing than others. In some cases there was more water loss than others. This together with differing amounts of cations from the abrasive which passed into solution resulted in the toothpastes having differing electrolyte concentrations. In each case the surfactant was present in the toothpaste in the form of a liquid crystal phase but the lamellar spacings were different for the different toothpastes as a consequence of the differing electrolyte concentration of the aqueous phase of the final products. In the manufacture of the toothpastes of this Example, and of those of all subsequent Examples, the ingredients are mixed at a temperature within the range 22° to 32° C. The values for the lamellar spacing, $d_o$, are given in Table I below. These values, and all other $d_o$ values given herein, are those determined within a month of manufacture of the respective toothpaste.

Also given in Table I are PG values for the respective products. PG stands for Plaque Growth and the smaller the PG value the greater the efficacy of the toothpaste to inhibit the growth of plaque on the teeth. The PG value is determined from data obtained when following a standard procedure for the measurement of plaque growth. The methodology of measuring plaque growth is that according to Harrap as described in J.Clin.Periodontol., 1974, 1, 166–174 which gives a procedure for assessing the amount of plaque on the teeth adjacent to the gingival margin. The procedure is as follows:

During the late afternoon each subject brushes his teeth with a simple, non-active paste (having a composition as given hereinafter) for an unspecified period of time to remove as much plaque as possible. This is immediately followed by brushing for one minute with 1.5 g of the allocated test paste. Residual paste is removed by rinsing the mouth with water and any remaining plaque disclosed by painting the teeth with an aqueous solution of Erythrosin (0.5% w/w) using a soft camel hair brush. Excess dye is removed by rinsing with water and the amount of plaque assessed and recorded for each of 16 teeth (numbers 3 to 6 for each quadrant). The recorded plaque is designated $P_0$.

No further oral hygiene is permitted for 18 hours after which time each subject rinses his mouth with water to remove food debris and viscous saliva. Plaque assessment is then carried out as before and recorded ($P_{18}$). The values of $P_{18}-P_0$ for each tooth are averaged to give a $P_{18}-P_0$ value per mouth. The mean of the values obtained for the subjects in the test is the PG value. Panels of at least 12 subjects are used. The Plaque Growth value for a toothpaste without active ingredients is usually in the range 22 to 26.

The composition of the simple, non-active toothpaste referred to above was the following:

| Ingredient | % |
|---|---|
| Alumina trihydrate | 50.00 |
| Glycerin | 27.00 |
| Hydroxyethylcellulose | 0.95 |
| Titanium dioxide | 0.50 |
| Water | to 100.00 |

The lamellar spacings and PG values for the toothpastes that were formulated are presented in Table I in the order of the magnitude of the lamellar spacings.

TABLE I

| Lamellar spacing of Liquid Crystal Sufactant Phase (nm) | PG Value |
|---|---|
| 6.6 | 19.9 |
| 6.3 | 18.5 |
| 6.1 | 16.8 |
| 5.6 | 16.1 |
| 5.0 | 15.6 |
| 4.8 | 14.5 |
| 4.6 | 13.4 |
| 4.3 | 12.4 |
| 4.0 | 12.0 |

This shows that as the $d_o$ value decreases the effectiveness of the toothpaste in inhibiting plaque growth increases.

The amounts of the liquid crystal surfactant phase for the above toothpastes all exceeded 1.5% by weight of the respective toothpaste.

EXAMPLE 2

This example shows the beneficial decrease in the PG value that can be obtained by the addition of a relatively minor amount of electrolyte.

Various toothpastes containing sodium chloride were made employing the ingredients listed in Table II.

TABLE II

| Ingredient | Toothpaste A | B | C |
|---|---|---|---|
| Alumina trihydrate | 50.000 | 50.000 | 50.000 |
| Sorbitol syrup (70%) | 27.000 | 27.000 | 27.000 |
| Sodium lauryl sulphate | 1.875 | 1.875 | 1.875 |
| Sodium dodecylbenzene sulphonate | 0.625 | 0.625 | 0.625 |
| Sodium carboxymethylcellulose | 0.850 | 0.850 | 0.800 |
| Zinc citrate trihydrate | 0.500 | 0.500 | 0.500 |
| Triclosan | 0.200 | 0.200 | 0.200 |
| Sodium chloride | 0.500 | 0.500 | 0.500 |
| Titanium dioxide | 0.500 | — | — |
| Sodium monofluorophosphate | 0.850 | 0.850 | 0.850 |
| Sodium saccharin | 0.180 | 0.180 | 0.180 |
| Formalin BP | — | 0.040 | 0.040 |
| Flavour oil | 1.200 | 1.200 | 1.200 |
| Water | to 100.000 | 100.000 | 100.000 |

Corresponding toothpaste A', B' and C' were made from which the sodium chloride was omitted.

The toothpastes of each pair of tootpastes A A', B,B' and CC' were made in an identical manner using the same mixer. The respective pairs were manufactured using commercial mixer types, respectively Thompson, Pressindustria and Fryman mixers.

Table III shows that in each case the inclusion of the sodium chloride resulted in an improvement in effectiveness in Inhibiting plaque growth.

TABLE III

| Toothpaste Pair | Difference in $d_o(nm)^1$ | Difference in PG values[2] |
|---|---|---|
| A,A' | 3.5 | 6.3 |
| B,B' | 3.1 | 5.6 |
| C,C' | 3.3 | 4.3 |

[1] the salt-containing toothpastes comprised surfactant liquid crystal phase with smaller $d_o$ values than the respective toothpastes not containing salt
[2] the salt-containing toothpastes gave lower PG values than the respective toothpastes not containing salt The amount of the liquid crystal surfactant phase in each of the six toothpastes exceeded 2% by weight.

EXAMPLE 3

A toothpaste was made from the same ingredients as for toothpaste A of Example 2 save that in place of Triclosan was employed the following antimicrobial agent:

| Toothpaste | Antimicrobial agent |
|---|---|
| D | 2,2'-methylenebis(3,4,6-trichlorophenol) |

Table IV gives the $d_o$ value, percentage weight of the liquid crystal surfactant phase and PG value for the toothpaste.

TABLE IV

| Toothpaste | $d_o$ (nm) | % wt liquid crystal phase | PG value |
|---|---|---|---|
| D | 4.1 | 3.7 | 11.5 |

EXAMPLE 4

This example illustrates the use of further antimicrobial agents.

Toothpastes were formulated as for toothpaste C of Example 2, or toothpaste A as indicated, save that the antimicrobial agents listed in Table V were used in place of Triclosan. The lamellar spacings, $d_o$, of the liquid crystal surfactant phase of each toothpaste is also given in Table V along with the percentage weight of the liquid crystal surfactant phase.

TABLE V

| Antimicrobial Agent | $d_o(nm)$ | % wt liquid crystal phase |
|---|---|---|
| 3,4',5-tribromosalicylanilide | 4.1 | 3.0 |
| 3,4,4'-trichlorocarbanilide | 4.1 | 2.4 |
| bis(2-hydroxy-5-chlorophenyl) sulphide | 4.1 | 0.8 |
| 5-methyl-2-pentylphenol | 4.0 | 1.7 |
| 2,4-dichlorobenzyl alcohol | 4.2 | 1.6 |
| 4-chloro-3,5-dimethylphenol | 4.2 | 2.0 |
| 5-chloro-2-hydroxydiphenyl methane | 3.9 | 0.9 |
| 5-n-octanoyl-3'-trifluoromethyl salicylanilide | 4.0 | 2.9 |
| n-butyl-p-hydroxybenzoate* | 3.6 | 3.8 |
| 2,2'-methylenebis(4-chloro-6-bromophenol)* | 4.0 | 4.0 |

*formulated as for toothpaste A of Example 2

EXAMPLE 5

This example shows that a wide variety of electrolytes can be used to lower the $d_o$ spacing of a liquid crystal surfactant phase of a toothpaste.

A series of toothpastes were made having the ingredients of toothpaste C of Example 2 save that the sodium chloride was replaced by another salt as indicated in Table VI below. This table also gives the $d_o$ spacings for the liqid crystal surfactant phase of each toothpaste, and the percentage weight of the liquid crystal surfactant phase.

TABLE VI

| Salt | % w/w | $d_o$ (nm) | % wt liquid crystal phase |
|---|---|---|---|
| Potassium chloride | 0.64 | 3.5 | 3.6 |
| Magnesium sulphate 7H₂O | 2.11 | 4.5 | 2.5 |
| Potassium lactate | 1.10 | 3.6 | 1.4 |
| Potassium tartrate 0.5H₂O | 1.01 | 3.7 | 2.1 |
| Sodium acetate | 0.70 | 3.5 | 3.0 |
| Sodium ascorbate | 1.69 | 3.8 | 3.2 |
| Sodium lactate | 0.96 | 3.8 | 3.0 |
| Sodium sulphate | 0.61 | 4.2 | 2.9 |
| Trisodium citrate 2H₂O | 0.84 | 3.6 | 3.0 |
| Potassium gluconate | 2.00 | 3.3 | 1.7 |
| Disodium hydrogen orthophosphate 12H₂O | 1.53 | 3.9 | 3.4 |
| Potassium acetate | 0.84 | 3.6 | 1.2 |
| Sodium glycinate 1H₂O | 0.98 | 3.9 | 2.7 |
| Sodium gluconate | 1.87 | 3.9 | 2.2 |
| Sodium tartrate 2H₂O | 0.99 | 4.0 | 2.2 |

In each case the amount of salt incorporated was equivalent to the same molar cation concentration as 0.5% sodium chloride.

The $d_o$ values for toothpastes C and C' were 3.9 nm and 7.2 nm, respectively.

EXAMPLE 6

This example shows the effect on the lamellar spacing of a liquid crystal surfactant phase of a dentifrice of including increasing amounts of sodium chloride in the dentifrice formulation up to 1% by weight of the dentifrice. The dentifrice comprised the following ingredients.

| Ingredients | % |
|---|---|
| Alumina trihydrate | 50.000 |
| Sorbitol Syrup (70% solution) | 27.000 |
| Sodium lauryl sulphate | 1.875 |
| Sodium docecylbenzene sulphonate | 0.625 |
| Sodium carboxymethylcellulose | 0.800 |
| Zinc citrate trihydrate | 0.500 |
| Triclosan | 0.200 |
| Sodium monofluorophosphate | 0.850 |
| Sodium saccharinate | 0.180 |
| Formalin BP | 0.040 |
| Flavour oil | 1.200 |
| Sodium chloride | see Table |
| Water | To 100.000 |

The $d_o$ values are given in Table VIII together with percentage weights of the liquid crystal phase.

TABLE VII

| % sodium chloride | $d_o$ (nm) | % wt liquid crystal phase |
|---|---|---|
| 0.000 | 7.5 | 2.1 |
| 0.100 | 7.4 | 2.0 |
| 0.200 | 6.4 | 1.4 |
| 0.300 | 4.8 | 1.1 |
| 0.400 | 4.1 | 1.0 |
| 0.500 | 4.1 | 1.1 |
| 1.000 | 3.8 | 1.7 |

All the toothphases were made in the same way, the amount of the sodium chloride being the only variable.

EXAMPLES 7 to 11

The following are further examples of dentifrice formulations of the invention that have been made.

| Ingredient Example: | 7 | 8 | 9 | 10 | 11 |
|---|---|---|---|---|---|
| Alumina trihydrate | 50.000 | 50.000 | 50.000 | 50.000 | — |
| Silica xerogel (Gasil 200) | — | — | — | — | 10.000 |
| Precipitated silica (Sipernat 22S) | — | — | — | 8.000 | — |
| Sorbitol syrup (70%) | 27.000 | 27.000 | 27.000 | 27.000 | 45.500 |
| Sodium lauryl sulphate | 1.875 | 2.500 | 1.875 | 1.875 | 2.400 |
| Sodium dodecylbenzene sulphonate | 0.625 | 0.500 | 0.625 | 0.625 | 0.800 |
| Sodium carboxymethylcellulose | 0.850 | — | 0.800 | 0.800 | 0.800 |
| Xanthan gum | — | 1.000 | — | — | — |
| Zinc citrate trihydrate | 1.000 | 0.500 | 0.500 | — | 0.500 |
| Sodium zinc citrate preparation[1] | — | — | — | 2.785 | — |
| Triclosan | 0.200 | 0.120 | 0.200 | 0.500 | 0.200 |
| Sodium chloride | 0.500 | — | — | — | 1.000 |
| Titanium dioxide | 0.500 | 1.000 | — | — | — |
| Sodium monofluorophosphate | 0.850 | 1.200 | 0.850 | 0.850 | 1.120 |
| Sodium saccharin | 0.180 | 0.180 | — | 0.180 | 0.300 |
| Sodium cyclamate | — | — | 2.000 | — | — |
| Formalin BP | 0.040 | 0.040 | 0.040 | 0.040 | — |
| Flavour oil | 1.200 | 1.200 | 1.200 | 1.200 | 1.200 |
| Colour | 0.008 | 0.007 | — | — | — |
| Water to | 100.000 | 100.000 | 100.000 | 100.000 | 100.000 |

[1] an aqueous premix of 1.41% trisodium citrate dihydrate and 1.375% zinc sulphate heptahydrate

| Example: | 7 | 8 | 9 | 10 | 11 |
|---|---|---|---|---|---|
| $d_o$ spacing (nm) | 4.0 | 3.9 | 3.8 | 3.7 | 3.5 |
| Plaque growth value | 12.7 | 13.1 | — | 10.7 | — |
| % wt liquid crystal phase | 3.8 | 2.7 | 2.6 | 3.0 | 10.0 |

EXAMPLES 12 to 14

The following are yet further examples of dentifrice formulations of the invention.

| Ingredient Example: | Parts by weight 12 | 13 | 14 |
|---|---|---|---|
| Alumina trihydrate | 50.00 | 50.00 | 50.00 |
| Sorbitol syrup (70%) | 27.00 | 27.00 | 27.00 |
| Sodium lauryl sulphate | — | 1.50 | 0.75 |
| Sodium dodecylbenzene sulphonate | 2.00 | — | 0.75 |
| Zinc citrate trihydrate | 1.00 | 1.00 | 1.00 |
| Triclosan | 0.50 | 0.50 | 0.50 |
| Sodium chloride | 1.00 | 0.50 | 1.00 |
| Sodium monofluorophosphate | 0.85 | 0.85 | 0.85 |
| Sodium saccharin | 0.20 | 0.20 | 0.20 |
| Formalin BP | 0.04 | 0.04 | 0.04 |
| Flavour oil | 1.20 | 1.20 | 1.20 |
| Water | 9.91 | 9.90 | 11.91 |
| $d_o$ spacing (nm) | 3.4 | 3.8 | 3.6 |
| % wt liquid crystal phase | 0.3 | 3.1 | 2.1 |

EXAMPLE 15

This example shows that toothpastes having surfactant present in the form of a liquid crystal phase with low $d_o$ spacing result in a superior retention of an antimicrobial agent on the teeth than do toothpastes for which the $d_o$ value is higher.

In this in vitro procedure human molar teeth were used. The area of tooth exposed to the test toothpaste was standardised as follows. Each tooth was cut in half vertically and each half was covered in wax, applied with a camel hair brush, with the exception of a 6 mm² window left uncovered on the enamel surface of each half tooth.

Toothpastes were delivered as 50% (w/v) slurries prepared freshly on the day of the test as follows. The diluent used was a mixture of ethanol and water (1:2 v/v) with ³H-Triclosan dissolved to give a final level of Triclosan in the toothpaste/diluent slurry of 20% greater than the total content of the paste being tested. For example, 5 g of a formulation containing 2 mg Triclosan/g paste (i.e. 10 mg Triclosan) was slurried with 5 ml of the ethanol/water mix containing an additional 2 mg ³H-Triclosan.

The volume of the test slurry used in each case was 30 μl; this was sufficient to cover the tooth window and was applied for 1 minute. After this application the tooth was washed for 45 seconds in water (2 ml). The wax was then removed and discarded, and the tooth washed further, twice in ethanol (2 ml) for 45 seconds and once in acidified ethanol (2 ml:conc HCl/ethanol 1/9 v/v) for 30 minutes. The radioactivity collected in the final two ethanol rinses and in the acid ethanol wash was measured in a Packard Tricarb 4530 Scintillation Counter with appropriate quench correction, using Insta-gel Liquid Scintillation Cocktail (United Technologies Packard). This was then expressed as the quantity of Triclosan binding to the tooth surface in the exposed window.

Appropriate control experiments demonstrated that radioactivity did not penetrate the wax covering of the tooth surface. The binding of Triclosan to the wax was ignored: the wax served simply as a shield and measurement of uptake was by the set area of tooth exposed by the wax window.

The results are summarised in Table VIII which represent the mean of nine determinations for each toothpaste.

TABLE VIII

| Toothpaste | Triclosan Content (%) | $d_o$ (nm) | Triclosan uptake (μg/6 mm² tooth surface) |
|---|---|---|---|
| Example 2A | 0.2 | 4.0 | 1.36 ± 0.16* |
| Example 2A' | 0.2 | 7.4 | 0.87 ± 0.04* |
| Example 1 | 0.5 | 4.0 | 1.28 ± 0.13** |
| Example 1 | 0.5 | 6.3 | 0.89 ± 0.11** |

*values significantly different at the 5% level
**values significantly different at the 5% level The batches of toothpastes 2A and 2A' used in this experiment were different from those for which data are given in Table III.

EXAMPLE 16

This example concerns the firding that the amount of zinc retained in the mouth after use of a toothpaste containing zinc citrate is greater for those toothpastes of which the lamellar spacing of the liquid crystal surfactant phase is the smaller.

Nineteen panellists rinsed an aqueous slurry of toothpaste (1 g toothpaste, 4 ml water) around the mouth for one minute. After this was expectorated and collected, a one minute 10 ml water rinse was carried out and collected. By analysis it was determined what proportion of the zinc in the toothpaste was retained in the mouth after the rinsing.

The two toothpastes employed had the formulation given in Example 1.

The results are given in Table IX.

TABLE IX

| $d_o$(nm) | % Zinc Retained in the mouth |
|---|---|
| 4.0 | 26%* |
| 6.3 | 6%* |

*values significantly different at the 5% level

Demonstration of long term plaque reduction and gum health benefit

The toothpaste used in this study was that of Table 1 having a $d_o$ spacing of 4.3 nm.

The effect of the extended use of a dentifrice containing 1 % zinc citrate and 0.5 % Triclosan on plaque accumulation and gingival health was investigated.

The study was divided into two parts, i.e. a four-week prestudy period to reduce the influence of motivation and professional cleaning was followed by a ten-week experimental period. During the prestudy period, the participants used a placebo dentifrice which had the same composition as the test toothpaste except that the zinc citrate and Triclosan were omitted. The ten-week experimental period was divided into two four-week periods, separated by a two-week interval. During the two four-week experimental periods the participants used the test and placebo dentifices in a double blind crossover design experiment. The two-week interval was adopted in order to minimise the influence of carry-over effects.

Volunteers were screened prior to participation in the study. The screening procedure was as follows. The partial recording scheme recommended by Cowell et al in J Clinical Periodontology, 1975, 2, 231-240 was used to select panellists in which the six specific teeth concerned were free of overt caries and had associated pocket depths of less than 3.5 mm when probed using the WHO probe(WHO stands for World Health Organisation). In addition, selected subjects had to exhibit at least a minimal level of gingival inflammation (more than 7 bleeding points out of 24 sites) to allow the demonstration of any improvement. Twenty males and twenty-nine females aged between 23 and 55 years participated in the study. No oral hygiene instructions were given but the participants were encouraged to use sufficient dentifrices to cover the head of the toothbrush (approximately 1.5 g).

Plaque was assessed using the Plaque Index according to Silness and Loe (Acta Odont.Scandinavia, 1964. 22, 121-35). Gingival inflammation was assessed by the Gingival Index described by Loe (J. Periodontology, 1967 38, 610-16) and a modification of the Bleeding Index suggested by Cowell et al (J.Clinical Periodontology, 1975, 2, 231-240). Pocket depths were recorded using 0.5 mm graduated plasticstrips 1.0 mm in width (Smith, British Dental J., 1975, 139, 369). Assessments were performed on the buccal, mesial, distal and lingual surfaces of representative teeth (2 molars, 2 premolars and 2 incisors) as suggested by Ramfjord (J. Periodontology, 1959, 30, 51–59).

First, the teeth were professionally cleaned to remove all traces of supra and subgingival plaque and calculus. The participants were then provided with placebo dentifrice and new brushes. The teeth were also professionally cleaned at the second examination which formed the baselines for the first experimental period of the crossover. The Bleeding and Plaque data recorded at this examination were used to allocate the panellist to one of the groups so that the two balanced groups were formed (Table X). One group was provided with the test dentifrice and the other group with the placebo, each to be used for four weeks. Following this period, the clinical parameters were reassessed and the placebo dentifrice was used for two weeks to avoid any carry-over effects arising from the test dentifrice prior to the second phase of the crossover. Clinical examination and professional cleaning preceeded the second experimental phase. Each participant was then given their second dentifrice. Participants were again examined at the end of this period.

The means of the plaque, gingival and bleeding indices for the four-week prestudy period are given below in Table X.

TABLE X

| | Plaque Index | Gingival Index | Bleeding Index |
|---|---|---|---|
| Baseline | 0.87 | 1.00 | 0.47 |
| Four-week | 0.77 | 0.99 | 0.49 |

The means of the plaque, gingival and bleeding indices for each four-week experimental period and for the overall study (n=41) for both dentifrices are given below in Table XI.

TABLE XI

| | End of First Experimental Period | End of Second Experimental Period | Mean of Total Group |
|---|---|---|---|
| Plaque Index | | | |
| Placebo | 0.91 | 0.91 | 0.91 |
| Test Dentifrice | 0.67 | 0.67 | 0.67 |
| Stat. signif.P> | 0.05 | 0.05 | 0.001 |
| Gingival Index | | | |
| Placebo | 0.92 | 0.93 | 0.92 |
| Test Dentifrice | 0.75 | 0.71 | 0.73 |
| Stat. signif.P> | 0.06 | 0.01 | 0.001 |
| Bleeding Index | | | |
| Placebo | 0.49 | 0.54 | 0.51 |
| Test Dentifrice | 0.39 | 0.42 | 0.41 |
| Stat. signif.P> | 0.09 | 0.01 | 0.001 |

The results shown in Table XI demonstrate a significant reduction in plaque accumulation and improvement in gingival health for the test dentifrice copared to the placebo.

Demonstration of enhanced inhibition of plaque metabolism

This study demostrates that a toothpaste composition according to the invention having a liquid crystal surfactant phase of low lamellar spaceing provides an enhanced inhibition of plaque metabolism compared with one having a liquid crystal surfactant phase of high lamellar spacing. Inhibition of plaque metabolism can be assessed by measuring the pH fall of plaque after a glucose rinse. The toothpastes used in this cross-over study were those of Table I having a $d_o$ spacing of 4.0 and 6.3 nm respectively, and were tested on ten panellists who refrained from toothbrushing for 24 hours prior to the experiment to allow plaque to accumulate. Each participant rinsed for 1 minute with 13 g of a 25% solution of the appropriate toothpaste in water. After 1 hour a plaque sample was collected, comprising of aliquots of plaque removed from at least eight incisor teeth. The pH of this sample dispersed in 5 $\mu$l deionised water was determined using an M1-410 Microcombination pH Probe (Microelectrodes Inc USA), the value being recorded 30 seconds after introduction of the pH electrode. The remaining plaque on the teeth was subjected to a 1 minute rinse with a 15% glucose solution. A second plaque sample was taken 5 minutes later and the pH measured as before. After an interval of 12 days the procedure was repeated with the panellists using the other test product.

The mean values for the pH drop caused by the glucose challenge after use of the test toothpastes are shown in Table XII. The smaller pH drop associated with the use of the product with the smaller $d_o$ value indicates that this toothpaste has a greater effect upon inhibition of plaque metabolism.

TABLE XII

| $d_o$ spacing of liquid crystal surfactant phase of toothpaste | Mean drop in plaque pH after glucose challenge |
|---|---|
| 4.0 nm | 0.57* |
| 6.3 nm | 0.84* |

*values significantly different at the 5% level.

What is claimed is:

1. A dentifrice composition, selected from the group consisting of a toothpaste, dental cream, or dental gel, effective to inhibit the growth of dental plaque comprising a surfactuant;

a particulate abrasive agent in an amount of between about 5 and 60% by weight of the dentifrice composition;

water in an amount between about 25 and 60% by weight of the dentifrice excluding insoluble solids; and an anti-plaque agent consisting of an effective amount of a substantially water-insoluble non-cationic antimicrobial agent or mixture thereof with a zinc salt having a water solubility greater than $2 \times 10^{-4}$ per 100 g of water at 25° C. and pH7, characterized in that there is present in the dentifrice composition a lamellar liquid crystal surfactant phase having a lamellar spacing of less than 6.0 nm in an amount of at least about 0.2% by weight of the dentifrice composition, the lamellar spacing and percentage weight of the lamellar liquid crystal surfactant phase being measured after a centrifugation separation procedure, said separation procedure comprising:

(1) sufficient centrifugation to separate the dentifrice composition into its main phases including a liquid portion; followed by (2) sufficient ultracentrifugation of the liquid portion so that the liquid portion separates into layers and there is no substantial change in the volumes of the separated layers of the liquid portion, the lamellar liquid crystal surfactant phase being present as one of the separated layers of the liquid portion.

2. A dentifrice composition as claimed in claim 1, wherein the lamellar spacing of the liquid crystal surfactant phase is less than 5.0 nm.

3. A dentifrice composition as claimed in claim 2, wherein the said lamellar spacing is less than 4.4 nm.

4. A dentifrice composition as claimed in claim 1, wherein said lamellar liquid crystal surfactant phase is present in an amount of at least 0.3% by weight of the dentifrice composition.

5. A dentifrice composition as claimed in claim 4, wherein said lamellar liquid crystal surfactant phase is present in an amount of at least 0.5% by weight of the dentifrice composition.

6. A dentifrice composition as claimed in claim 1, wherein the surfactant is an anionic surfactant.

7. A dentifrice composition as claimed in claim 6, wherein the surfactant is selected from the group consisting of sodium lauryl sulphate, sodium dodecylbenzene sulphonate, sodium lauroyl sarcosinate and mixtures thereof.

8. A dentifrice composition as claimed in claim 1, wherein the particulate abrasive agent is selected from alumina and silica abrasives having a particle size in the range of 2 to 20 microns.

9. A dentifrice composition as claimed in claim 1, wherein in the formulation of the dentifrice there is also included as an ingredient from 0.1 to 3% by weight of sodium chloride or a water-soluble electrolyte salt, other than a fluorine-containing salt, in an equivalent molar cation concentration effective to reduce the lamellar spacing of the liquid crystal surfactant phase to below 6.0 nm, but in an amount insufficient to result in the destruction of the liqid crystal surfactant phase.

10. A dentifrice composition as claimed in claim 9, wherein in the fromulation of the toothpaste there is included 0.1 to 1% by weight of sodium chloride.

11. A dentifrice composition as claimed in claim 1, wherein the antimicrobial agent is selected from the group consisting of phenolic compounds, bisphenolic compounds, halogenated diphenyl ethers, benzoate esters and carbanilides.

12. A dentifrice composition as claimed in claim 1, wherein the antimicrobial agent has a solubility in water at 25° C. of less than 0.5%.

13. A dentifrice composition as claimed in claim 12, wherein the antimicrobial agent has a solubility in water at 25° C. of less than 0.1%.

14. A dentifrice composition as claimed in claim 11, wherein the antimicrobial agent is Triclosan.

15. A dentifrice composition as claimed in claim 1, wherein the antimicrobial agent is present in an amount of 0.01 to 5% by weight.

16. A dentifrice composition as claimed in claim 1, wherein the zinc salt has a water solubility greater than $1 \times 10^{-2}$ g per 100 g of water at 25° C. and pH 7.

17. A dentifrice composition as claimed in claim 1, wherein the zinc salt is a salt of an orgainic acid selected from mono-, di-, and tri-carboxylic acids, alphahydroxy carboxylic acids and amino acids.

18. A dentifrice composition as claimed in claim 17, wherein the zinc salt is zinc citrate.

19. A dentifrice composition as claimed in claim 1, wherein the zinc salt is present in such amount as to provide from 0.05 to 1.5% of zinc by weight of the composition.

20. A dentifrice composition as claimed in claim 1, comprising 0.05 to 3% Triclosan, 0.3% to 1.5% zinc citrate, 0.2 to 1% sodium chloride and 1 to 3% sodium lauryl sulphate.

21. A dentifrice composition as claimed in claim 1, comprising agout 1% to about 3% by weight of an anionic surfactant selected from the group consisting of sodium lauryl sulphate, sodium dodecylbenzene sulphonate, sodium lauroyl sarcosinate and mixtures thereof, an anti-plaque agent consisting of from about 0.01% to about 5% by weight Triclosan or a mixture of said Triclosan with about 0.2% to about 2% by weight zinc citrate, about 0.1% to about 3% by weight sodium chloride, about 5% to about 60% by weight of an abrasive selected from alumina and silica abrasives, about 15% to 70% by weight of sorbitol syrup and about 0.1% to 5% by weight of flavour oil.

22. A dentifrice composition as claimed in claim 1, wherein the lamellar spacing is measured within a mouth of manufacturing the dentifrice composition.

* * * * *